United States Patent [19]

Fawzi et al.

[11] 4,440,738

[45] Apr. 3, 1984

[54] STABLE RADIOGRAPHIC IMAGING AGENTS

[75] Inventors: Mahdi B. Fawzi, Fairfield; James J. Benedict, Cincinnati; Joseph E. Bugaj, Harrison; Charles R. Degenhardt, Cincinnati; Barry F. Van Duzee, Westchester, all of Ohio

[73] Assignee: Mallinckrodt, Inc., St. Louis, Mo.

[21] Appl. No.: 387,138

[22] Filed: Jun. 10, 1982

[51] Int. Cl.$^3$ .................. A61K 49/00; A61K 43/00
[52] U.S. Cl. .......................................... 424/1.1; 424/9; 252/397; 252/399; 252/401; 252/404
[58] Field of Search ................ 424/1, 1.5, 9; 252/82, 252/86, 397, 399, 400 A, 401–404

[56] References Cited

U.S. PATENT DOCUMENTS

| | | | |
|---|---|---|---|
| 2,832,689 | 4/1958 | Proctor et al. | 424/1 |
| 3,735,001 | 5/1973 | McRae et al. | 424/1 |
| 3,735,295 | 4/1973 | Eckelman et al. | 424/1 |
| 4,054,645 | 10/1977 | Hill et al. | 424/1 |
| 4,104,366 | 8/1978 | Schmidt-Dunker et al. | 424/1 |
| 4,115,541 | 9/1978 | Subramanian et al. | 424/1 |
| 4,229,427 | 10/1980 | Whitehouse | 424/1 |
| 4,233,284 | 11/1980 | Fawzi | 424/1 |
| 4,247,534 | 1/1981 | Bevan | 424/1 |

FOREIGN PATENT DOCUMENTS

| | | | |
|---|---|---|---|
| 46067 | 2/1982 | European Pat. Off. | 424/1 |
| 47983 | 3/1982 | European Pat. Off. | 424/1 |
| 54195 | 6/1982 | European Pat. Off. | 424/1 |
| 1489330 | 10/1977 | United Kingdom | 424/1 |
| 1541070 | 2/1979 | United Kingdom | 424/1 |

*Primary Examiner*—Christine M. Nucker
*Attorney, Agent, or Firm*—Bernard, Rothwell & Brown

[57] ABSTRACT

Stable compositions, useful as technetium-99m-based imaging agents, comprise reductic acid or certain structurally-related compounds in combination with a pertechnetate reductant or dissolved in pertechnetate-99m solution. The compositions are especially useful, in combination with a phosphate or phosphonate bone-targeting carrier, for skeletal imaging.

18 Claims, No Drawings

STABLE RADIOGRAPHIC IMAGING AGENTS

BACKGROUND OF THE INVENTION

This invention relates to compositions useful in the preparation of radiodiagnostic agents for use in tissue imaging. More particularly, it relates to compounds used as non-interfering stabilizers for such compositions.

Scintigraphic skeletal imaging and similar radiographic techniques for visualizing other tissues are finding ever-increasing application in biological and medical research and in diagnostic procedures. Generally, scintigraphic procedures involve the preparation of radioactive agents which, upon introduction into a biological subject, become localized in specific organs, tissues, or skeletal structures that are under study. When so localized, traces, plots, or scintiphotos of the distribution of the radiographic materials can be made by various radiation detectors, e.g., transversing scanners and scintilation cameras. The distribution and corresponding relative intensity of the detected radioactive material not only indicates the position occupied by the tissue in which the radionuclide is localized, but also indicates the presence of aberrations, patholidical conditions, and the like.

In general, depending on the type of radionuclide used and the organ of interest, a scintigraphic imaging agent as used in a hospital comprises a radionuclide, a carrier agent designed to target the specific organ, various auxiliary agents which affix the radionuclide to the carrier, water or other delivery vehicles suitable for injection into, or aspiration by, the patient, physiologic buffers and salts, and the like. The carrier attaches or complexes with the radionuclide, and localizes the material in the location where the carrier naturally concentrates in a biologic subject. Certain radionuclides may be used without an additional carrier, such as thallium-201 ($^{201}$Tl) and technetium-99m ($^{99m}$Tc), in pertechnetate form, for brain and thyroid imaging.

Technetium-99m is widely known for use in tissue imgaging agents. This radionuclide is conveniently available commercially in the oxidized pertechnetate form ($^{99m}$TcO$_4^-$, hereinafter "pertechnetate-Tc99m"). However, the technetium in pertechnetate has a valence state of +7 and, thus, will not complex with the most commonly used carriers for radionuclide tissue imaging. This problem is easily overcome by reducing the technetium to what is believed to be the +3, +4, and/or +5 oxidation state. Thus, technetium-labeled imaging agents are generally prepared by admixing pertechnetate-Tc99m isotonic saline solution with a technetium reductant (reducing agent) such as the stannous, ferrous, or chromous salt of sulfuric or hydrochloric acid, and the desired carrier agent for targeting the organ of interest. For example, organophosphonates are known as suitable carrier agents which target technetium radionuclide to bone tissue. U.S. Pat. No. 3,983,227, Tofe and Francis, discloses the use of reducing salts with radioactive pertechnetate-Tc99m solutions and organophosphonate bone-seeking carriers to prepare skeletal imaging agents.

Technetium-containing scintigraphic imaging agents are known to be unstable in the presence of oxygen, primarily since oxidation of the reductant and/or the technetium destroys the reduced technetium/targeting carrier complex. Accordingly, such imaging agents are generally made oxygen-free by saturating the compositions with oxygen-free nitrogen gas or by preparing the agents in an oxygen-free atmosphere. Stabilization of imaging agents can also be achieved through chemical means. U.S. Pat. No. 4,232,000, Fawzi, issued Nov. 4, 1980, discloses the use of gentisyl alcohol as a stabilizer for technetium imaging agents. Similarly, U.S. Pat. No. 4,233,284, Fawzi, issued Nov. 11, 1980, discloses the use of gentisic acid as a stabilizer. German Offenlegungsschrift No. 2,618,337, Tofe, published Nov. 11, 1976, discloses the use of ascorbic acid and erythorbic acid as stabilizers with technetium imaging agents.

Commercial products for use in skeletal imaging are generally provided in liquid or dry powder mixture "kits" with vials containing phosphate or phosphonate bone seeking carriers. Skeletal imaging agents are formed by adding pertechnetate-Tc99m, in physiological saline, to such kits.

It has now been discovered that redutic acid and certain compounds structurally-similar to reductic acid are safe, effective, non-interfering stabilizers for agents used in tissue imaging. In a specific mode, phosphate or phosphonate-containing imaging kits containing such stabilizers yield stable imaging agents.

SUMMARY OF THE INVENTION

The present invention provides highly stable compositions useful in the preparation of imaging agents containing technetium-99m. The compositions of the present invention comprise a pertechnetate reductant or oxidized pertechnetate solution and a stabilizing amount of reductic acid, certain structurally-related compounds, and pharmaceutically-acceptable salts, esters, amides, and mixtures thereof, (hereinafter referred to as "reductate stabilizers"). Another composition further comprises a carrier that targets the technetium-99m to a specific organ or tissue to be imaged. In a method aspect, the present invention encompasses an improved method of preparing a technetium-based imaging agent comprising codissolving a pertechnetate reductant and a reductate stabilizer, in a pertechnetate-Tc99m solution. In preferred embodiments of this invention, 6-halogen substituted ascorbic acid compounds, substituted teductic acid compounds, and/or nicotinamide complexes thereof are incorporated as stabilizers.

DESCRIPTION OF THE INVENTION

Materials which are useful stabilizers for radiodiagnostic agents must exhibit the following properties:

(1.) Toxicological acceptability under the conditions of use;

(2.) The ability to stabilize the product for a reasonable period of storage and/or under use conditions; and (3.) No substantial interference with the delivery of the radionuclide to the intended organ.

The present invention is based on the discovery that reductate stabilizers meet all of the above three criteria for a stabilizer.

There are several compositional aspects to the present invention. In one aspect, compositions of the present invention comprise a pertechnetate reductant which provides a pertechnetate-reducing metal or cation, and the reductate stabilizer. In a second aspect, the compositions of the present invention comprise a pertechnetate-Tc99m solution having dissolved therein a stabilizing amount of the reductate stabilizer.

When practicing the present invention, it is not critical which of these compositional forms is used to prepare the final technetium-based imaging agent. Commercial producers of pertechnetate generators may find it desirable to dissolve low levels of the reductate stabilizer directly into the pertechnetate solution as it is eluted from the generator, or to incorporate a reductate stabilizer directly on the generator column. Alternatively, it may be more convenient to combine the reductate stabilizer with the pertechnetate reductant. In either case, upon combining the pertechnetate solution with the pertechnetate reductant and recudtate stabilizer, an improved, highly stable imaging agent is provided.

As used herein, the term "imaging" refers to all radiographic tissue imaging processes for which the instant compositions may be used, including (but not limited to) skeletal imaging. The term "imaging agent" refers to compositions useful for tissue imaging, including (but not limited to) skeletal imaging, such compositions comprising the product of admixing pertechnetate-Tc99m, or other useful radioisotope, to an imaging kit at least comprising a pertechnfnetate reductant, and reductate stabilizer.

Another composition of this invention further comprises a tissue-targeting carrier which attaches/complexes with technetium-99m and localizes the radionuclide in a particular body organ or tissue. One preferred aspect of such a composition comprises a tissue-targeting carrier, pertechnetate reductant, and a reductate stabilizer in an "imaging kit" or "kit," as referred to herein. An imaging agent, then, is formed by addition of a pertechnetate-Tc99m solution.

Kits, and other compositions of this invention for use commercially, preferably contain sufficient material to form multiple doses of imaging agent. Obviously, the amount of material to be incorporated in such compositions will depend upon the number of doses of imaging agent desired. Further, specific quantities of pertechnetate reductant, reductate stabilizer, and optional carrier may vary according to the particular compound used. The practitioner of this invention may determine appropriate quantities by reference to literature describing particular carriers and reductants. Components useful in forming the imaging kits, and other compositional forms of this invention, are described below.

Components

Reductate Stabilizers:

The compositions of the instant invention incorporate a reductate stabilizer. These stabilizers are compounds and mixtures of compounds of the formula

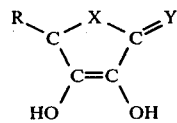

wherein X is CRR', O, or NR' is hydrogen, or lower alkyl (containing from 1 to 8 carbon atoms), Y is oxygen, sulfur, nitrogen or $CH_2$; R is hydrogen, lower alkyl containing from 1 to 8 carbon atoms, alkyl containing from 3 to 8 carbon atoms substituted with one or more hydroxy, halogen, amino, or thiol groups, lower alkyl containing from 1 to 8 carbon atoms halogen-substituted on the first and/or second carbon atom; lower alkenyl (containing from 2 to about 8 carbon atoms); nicotinic acid and nicotinamide complexes thereof and pharmaeutically-acceptable salts, esters, and amides thereof. Syntheses of these compounds are described in the following literature, incorporated by reference herein: Bock, et al., *Carbohydrate Research*, 68, 313–319 (1979); Cousins, et al., *Journal of the American Oil Chemists Society*, 54, 308–312 (1977); Feather, et al., *Journal of Organic Chemistry*, 31, 4018–4021 (1966); and Wenner, *Journal of Organic Chemistry*, 14, 22–26 (1949).

Preferred compounds of formula (I) include halogen-substituted ascorbic acids of the formula:

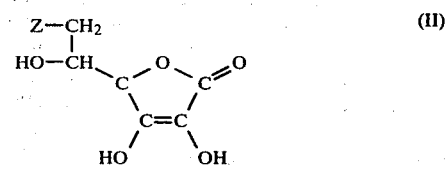

wherein Z is halogen. Compounds of this formula (II) include 6-bromo-6-deoxyascorbic acid, 6-chloro-6-deoxyascorbic acid, and 6-iodo-6deoxyascorbic acid.

Another class of preferred comounds of formula I include compounds of the formula:

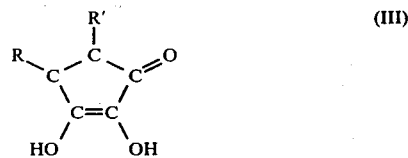

wherein R and R' are as defined above. Compounds of this formula (III) include reductic acid, 4-methyl reductic acid, 5-ethyl reductic acid, 5-methyl reductic acid, and 5-ethyl reductic acid.

A third group of preferred compounds include the nicotinamide complexes of compounds of formula (I); i.e.:

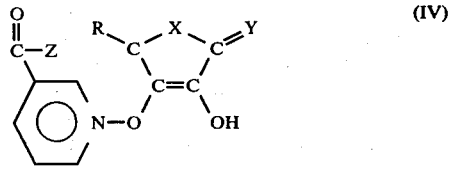

wherein X, Y, and R are as defined above, and Z is OH or $NH_2$. Compounds of this formula IV include nicotinic acid and nicotinamide complexes of 6-bromo-6-deoxyascorbic acid, 6-chloro-6-deoxyascorbic acid, reductic acid, and 5-methylreductic acid.

Preferred compounds of the formulae above have particular advantages over stabilizers currently known and used in the art. For example, 6-bromo-6-deoxyascorbic acid is a more effective stabilizer than ascorbic acid or erythorbic acid. (Ascorbic acid and erythorbic acid are stabilizers analagous to formula (II), above, wherein "Z" is hydroxyl; as described in German Offenlegungsschrift No. 2,618,337, Tofe, published Nov. 11, 1976.)

In pratice, the salt and ester forms of reductate stabilizers suitable for use in the present invention can be selected for use according to their solubility in a pertechnetate solution. It is, of course, preferable that the salts and esters be readily soluble in a pertechnetate solution. Accordingly, suitable salts include the alkali metal, alkaline earth metal, heavy metal and ammonium salts. The alkali metal salts such as sodium, potassium and lithium salts are readily soluble and accordingly prefered for use herein. Various ammonium salts, wherein the cation is N(R')$_4$ are also suitable for use herein. These include, for example, alkylammonium, alkanolamonium and arylammonium salts. It is of course, understood that the solubility of ammonium salts is largely dependent upon the number and nature of the substituent groups on the nitrogen atom. In general, and as used herein, preferred readily soluble ammonium salts include those wherein each R' is either hydrogen or $C_1$ to about $C_5$ hydrocarbyl. Nonlimiting examples of pharmaceutically-acceptable ammonium salts useful herein include the ammonium, methylammonium, dimethylammonium, tetramethylammonium, bis-(tetramethylammonium). 2-hydroxypropylammonium, bis-(2-hydroxypropylammonium), ethanolammonium, diethanolammonium, triethanolammonium, bis-(triethanolammonium), phenylammonium, naphthylammonium and quinolylammonium salts.

The alkaline earth metal salts, for example the calcium and magnesium salts, although less soluble, are also suitable for use herein. The heavy metal salts, for example the iron and tin salts, are also suitable for use herein.

The pharmaceutically-acceptable esters of the reductate stabilizers, readily soluble in pertechnetate solutions, include, for example, the $C_1$ to $C_{20}$ alkyl esters such as the methyl, ethyl, propyl, isopropyl, butyl, isobutyl, pentyl, hexyl, octyl, and palmityl esters. Pertechnetate reductants:

In embodiments of this invention in which the reductate stabilizers is combined with the pertechnetate reductant, the choice of reductant is not critical. As used herein the term "pertechnetate reductant" is intended to include compounds, complexes, or the like, comprising a reducing ion capable of reducing heptavalent technetium ($TcO_4^-$) to trivalent, tetravalent and/or pentavalent technetium. Free metals such as tin are also known for use a pertechnetate reductants, although undissolved metal must be removed from the imaging solution prior to infection into the patient. Thus, it is more convenient to use metal compounds which provide the reducing-metal cation in soluble form.

Suitable pertechnetate reductants can be combined with numerous adjuvants such as fillers and skeletal or other organspecific carriers. Skeletal imaging agents have been prepared utilizing metallic salts of sulfuric and hydrochloric acid such as stannous chloride, chromous chloride and ferrous sulfate as the pertechnetate reductant in combination with various organic phosphonates and/or phosphates as the bone seeking carrier. See, e.g., U.S. Pat. No. 3,983,227, Tofe, et al., issued Sept. 28, 1976 (incorporated by reference herein). Other systems capable of reducing pertechnetate-99m include, for example, acid-thiosulfates, acid-hydrogen-sulfates, iron colloids, and acid-borohydrides. U.S. Pat. Nos. 3,735,001 granted May 22, 1973; 3,863,004 granted Jan. 28, 1975; 3,466,361 granted Sept. 9, 1969; 3,720,761 granted Mar. 13, 1973; 3,723,612 granted Mar. 27, 1973; 3,725,295 granted Apr. 3, 1973; 3,803,299 granted Apr. 9, 1974; and 3,749,556 granted Jul. 31, 1973 (all incorporated herein by reference) disclose various pertechnetate reductants comprising reducing ions capable of reducing heptavalent pertechnetate to appropriate lower valence states.

Optional Carriers:

Compositions of the present invention may also contain compounds which complex with technetium radionuclide and localize the radionuclide in particular body tissues and organs. Broadly speaking, there are two classes of such carrier agents: those which target soft tissue organs such as the heart, marrow, liver, spleen, kidneys and lungs; and those which target calcified tissue, such as bone and other tissues which may be undergoing pathologicasl calcification. Examples of such carriers, or "targeting" agents for soft tissues include: colloidal sulfur, albumin, and the like. Targeting agents for bone mineral include the water-soluble phosphates, and (preferably) phosphonates.

Operable mono-, di-, and polyphosphonates particularly useful for skeletal imaging include compounds admixtures of compounds, selected from the group consisting of:

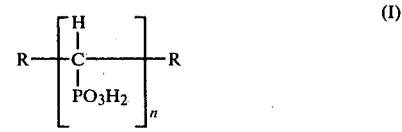
(I)

wherein each R is hydrogen or $CH_2OH$ and n is an integer of from 3 to 10;

(II)

wherein $R_1$ is hydrogen, alkyl containing from 1 to about 20 carbon atoms, amino alkyl, substituted aminoalkyl, alkenyl containing from 2 to about 20 carbon atoms, aryl (e.g., phenyl, napthyl), phenylethenyl, benzyl, halogen (e.g., chlorine, bromine and fluorine), hydroxyl, amino, substituted amino (e.g., dimethylamino, diethylamino, N-hydroxy-N-ethylamino, acetylamino), —$CH_2COOH$, —$CH(COOH)CH_2COOH$, —$CH_2PO_3H_2$, —$CH(PO_3H_2)(OH)$, or —$(CH_2C(PO_3H_2)_2)_n$—H where n=1 to 15, $R_2$ is hydrogen, lower alkyl (e.g., methyl, ethyl, propyl and butyl), amino, benzyl, halogen (e.g., chlorine, bromine, and fluorine), hydroxyl, —$CH_2COOH$, —$CH_2PO_3H_2$, or —$CH_2CH_2PO_3H_2$;

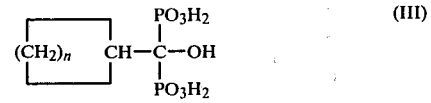
(III)

where n is an integer of from 3 to 9;

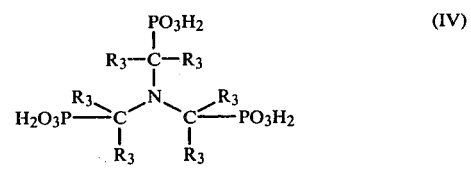
(IV)

wherein $R_3$ is hydrogen or lower alkyl (e.g.;, methyl, ethyl, propyl and butyl);

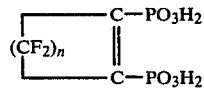 (V)

wherein n is an integer of from 2 to 4;

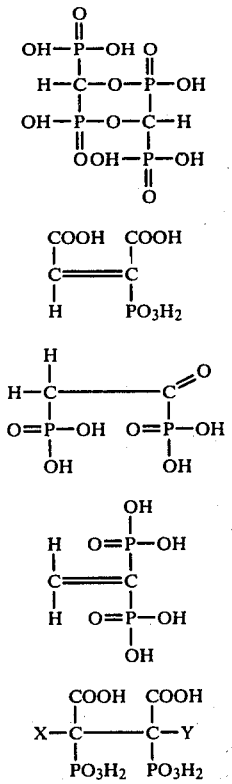

wherein X and Y are each hydrogen or hydroxyl; and the pharmaceutically-acceptable salts of each of the foregoing phosphonates. Suitable phosphonate salts for use with the present invention include sodium, potassium, ammonium and low molecular weight substituted ammonium (e.g., mono-di- and triethanolamine and quaternary ammonium) salts of the above phosphonates and mixtures thereof. Phosphonates and salts thereof are further described in U.S. Pat. No. 3,983,277, Tofe, et al., issued Sept. 28, 1976 incorporated by reference herein).

Preferred carriers for use herein include the diphosphonates of formula (II). Particularly preferred diphosphonates include methane diphosphonic acid (MDP), methane hydroxydiphosphonec acid (HMDP), and ethane-1-hydroxy-1,1-diphosphonic acid (EHDP). HMDP is a most preferred carrier. Also particularly preferred are amino diphosphonate compounds of the formulae:

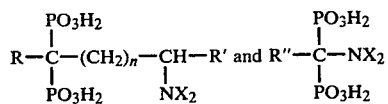

wherein n is an integer from 0 to 5; R is hydrogen, hydroxy, halogen, or amino; R' is hydrogen or alkyl containing from 1 to about 5 carbon atoms; R'' is hydrogen, halogen, alkyl containing from 1 to about 8 carbon atoms, or aryl; X is hydrogen, alkyl containing from 1 to about 8 carbon atoms, aryl, alkylaryl, acetyl, or haloaryl; and the pharmaceutically-acceptable salts thereof. These diphosphonates are further described in the following documents incorporated by reference herein: U.S. Pat. No. 4,247,534, Bevan, issued Jan. 27, 1981; U.S. Patent application Ser. No. 387,135, Benedict and Van Duzee, "Radiographic Imaging Agents," filed concurrently herewith; and U.S. Patent application Ser. No. 387,137, Van Duzee, "Radiographic Imaging Agents," filed herewith.

U.S. Pat. No. 4,016,249, issued Apr. 5, 1977, incorporated by reference herein, contains a succinct disclosure of the use of inorganic phosphates of various types in the manufacture of skeletal imaging agents. In particular, certain soluble pyrophosphate species having a molecular weight of less than about 300, said pyrophosphate containing no more than about 25% branched-chain polyphosphate, are quite useful for skeletal imaging. As with the organophosphonates, the pyrophosphate is conveniently used by admixture with a reducing salt for pertechnetate, thereby providing a kit. In use, the kit is charged with an aqueous solution of pertechnetate, whereupon the heptavalent technetium is reduced to a lower oxidation state, where it combines with the pyrophosphate. When injected into the patient the pyrophosphate targets bone mineral with the technetium radionuclide, in the manner of the organophosphonates.

Composition and Methods

The concentration of reductate stabilizer utilized in embodiments of this invention in which the stabilizer is combined with a reductant will vary depending upon the ultimate use of the composition and the concentration of inert or filler materials utilized. (All concentrations herein are defined as percentages by weight.) However, concentrations of the reductate stabilizer greater than about 25% interfere with the formation of an acceptable imaging agent and should be avoided. For most purposes concentrations in the range of about 0.1% to 5% are suitable.

Where it is desirable to incorporate the reductate stabilizer directly into the pertechnetate solution, the stabilizer can be simply dissolved either during or after elution of the pertechnetate generator. The elution process is thoroughly described in U.S. Pat. No. 3,369,121 (incorporated by reference herein).

In embodiments of the present invention in which the reductate stabilizer is dissolved in a pertechnetate solution, the concentration of stabilizer will vary depending upon the degree of saline dilution. It has been found that reductate stabilizer concentration greater than about 0.1% interferes with the formation of an acceptable imaging agent. Accordingly, for most purposes, a concentration no greater than 0.1% preferably no greater than 0.05%, by weight is suitable. A concentration within the range of from about 0.1% to about 0.001% is acceptable for many applications.

The present invention also encompasses an improved method of preparing technetium-based imaging agents comprising codissolving a reductate stabilizer and a pertechnetate reductant in a pertechnetate solution. As described above, the stabilizer and pertechnetate reductant may be either simultaneously dissolved or sequentially dissolved in the pertechnetate solution. Either codissolving procedure results in an improved technetium-based imaging agent.

In a preferred embodiment of the present invention, a stable technetium-based skeletal imaging agent can be formed by the direct addition of a pertechnetate solution to a compostion comprising: a pertechnetate reductant containing a metallic reducing ion in salt form, such as stannous chloride; from about 0.3% to about 1.5%, by weight, of a reductate stabilizer and a skeletal-specific carrier compound selected from the mono-, di- or polyphosphonates, as described above.

A particularly preferred aspect of this invention comprises:
(1) a diphosphonate carrier;
(2) a stannous reductant, and
(3) a reductate stabilizer;
wherein the molar ratio of diphosphonate to stannous tin is greater than or equal to about 65:1, preferably greater than or equal to about 75:1. (As used herein, "stannous tin" refers to elemental $Sn^{-2}$ contained in the reductant compound.) This "molar ratio" is the ratio of the number of moles of diphosphonate present in the composition to the number of moles of stannous tin present.

The quantity of these components incorporated into a preferred kit is enough to form multiple doses of imaging agent, as whe reconstituted with a pertechnetate solution containing about 1 to 400 millicuries (mCi) of technetium-Tc99m. (The number of doses ultimately obtained from such a kit depends upon such factors as the weight of the dosed subject and the type of tissue to be imaged.) Generally, then, a preferred kit comprises:
(a) an amount of diphosphonate carrier sufficient to the target the technetium in a pertechnetate solution containing from about 1 to 400 mCi of technetium-Tc99m;
(b) an effective amount of stannous reductant sufficient to reduce the technetium in a pertechnetate solution containing from about 1 to 400 mCi technetium-99m, and
(c) an amount of stabilizer sufficient to prevent oxidation of the reductant and the reduced technetium-99m.

See, e.g., the following U.S. Patent applications filed concurrently herewith, incorporated by reference: U.S. Patent application Ser. No 387,135, "Radiographic Imaging Agents," Benedict and Van Duzee; and U.S. Patent application Ser. No. 387,137, "Radiographic Imaging Agents," Van Duzee.

The imaging agents made with the kits of this invention are intended for intravenous injection into humans or lower animals. Accordingly, appropriate manufacturing and operating conditions are employed so as to provide suitably sterile, pyrogen-free compositions. Although not necessary to the practice of the present invention, it is preferable to use a pharmaceutically-acceptable extender or filler to dilute the reducing and diphosphonate salts in order to simplify metering the requisite small quantities of such salts. Sodium chloride and glucose are preferred; sodium chloride is especially preferred inasmuch as its addition will assure that the resulting agent is at least isotonic even if the pertechnetate-Tc99m solution is hypotonic (as is the case when it must be diluted with sterile water to reduce its activity.)

The kit compositional aspects of the present invention can be prepared by simply dry mixing the technetium reductant, the diphosphonate carrier, reductate stabilizer together with optional non-interfering agents such as sodium chloride. Such compositions are preferably placed in sterile vials fitted with a rubber septum, thereby facilitating mixing with a pertechnetate-Tc99m solution and convenient use in the hospital. The vials are preferably nitrogen-filed as an added protection against oxidation of the technetium reducing metal salt on storage.

In another mode, kits can be provided as aqueous solutions in sterile, pyrogen-free water. Preferably, the water is deoxygenated and the composition is stored under nitrogen, thereby minimizing undesirable oxidation of the pertechnetate reductant on storage.

In a preferred mode, the kit compositions can be provided in freeze-dried (lyophilized) form. Such compositions are prepared by co-dissolving the diphosphonate carrier and the pertechnetate reductant in an aqueoue solution, together with the present reductate stabilizers, and freeze-drying the composition using standard equipment. Preferably, sterile, deoxygenated water is used in processing and the product is stored under nitrogen. Although somewhat more complicated to manufacture than the dry mixture product, the freeze-dried product offers the advantage that water-insoluble particulate matter which might be present in the raw materials can be removed by filtration prior to the freeze drying step.

A preferred method of producing a lyophilized kit including the steps of:
(1) preparing an aqueous solution of diphosphonate carrier, reductant, and reductate stabilizer;
(2) adjusting the solution found in step 1 to a pH in the range from about 5.5 to about 6.5; and
(3) lyophilizing the pH-adjusted solutions.
Most preferably, the solution of step 1 is adjusted to about pH 6.0. The pH may be adjusted through the addition of a pharmaceutically-acceptable acid or base. This process is described in concurrently filed U.S. Patent application Ser. No. 387,136, "Process for Making a Lyophilized Product For Use In Skeletal Imaging," Van Duzee and Dugenhardt.

The kit compositions of this invention are dissolved with a pertechnetate-Tc99m isotonic solution from a commercial technetium source to yield an imaging agent suitable for intravenous injection. The stability of such imaging agents is ample under ordinary hospital conditions. Administration is preferably done within eight hours after addition of the pertechnetate-Tc99m solution. Preferably, the concentration, of reagents and technetium radionuclide is sufficient that about 1 milliliter of the solution is used in an adult of about 50–100 kg body weight. One milliliter of solution is preferably injected intravenously over a period of about 30 seconds. The total dosage of radionuclide for a sharp skeletal or myocardial infarct scan ranges from about 5 mCi to about 30 mCi, preferably from about 10 mCi to about 20 mCi. See also (incorporated by reference herein), U.S. Pat. No. 4,234,562, Tofe et al., issued Nov. 18, 1980; and U.S. Pat. No. 4,247,534, Bevan, issued Jan. 27, 1981.

The following non-limiting examples illustrate the composition, production, and use of the present invention.

EXAMPLE I

An imaging kit, encompassed by the present invention, was produced with the following ingredients:

| Component | Quantity in Bulk | Quantity in Kit |
|---|---|---|
| disodium salt of HMDP | 300. mg | 3.0 mg |
| stannous chloride | 3.2 mg | 0.032 mg |
| 6-bromo-6-deoxy-ascorbic acid | 81.0 mg | 0.081 mg |
| sodium chloride | 3000. mg | 30.0 mg |

The HMDP, stabilizer, and sodium chloride were dissolved in sterile, nitrogen-purged (deoxygenated) water. After dissolution of those components, the stannous chloride was dissolved in the solution. Sodium hydroxide was added to adjust the pH to 6.0. Sterile, deoxygenated water was added to bring the solution volume to 100 ml.

One milliliter aliquots of the solution were placed in sterile, nitrogen purged vials. The vials were then freeze-dried (lyophilized) in a commercial lyophilizer, stoppered and sealed.

An imaging agent is prepared using this kit by adding about 5 ml of a pertechnetate-Tc99m physiological saline solution, with an activity of about 75 mCi, from a commercial technetium source. The vial is agitated until the kit components are dissolved. About 1 ml of the agent is slowly injected, over a period of about 30 seconds, into an adult human subject weighing about 75 kg. Excellent skeletal images are then obtained using a scintillation camera.

In the kit prepared above, stannous fluoride and stannous sulfate respectively, are used instead of stannous chlorde, with substantially similar results. Also, in the foregoing kit, methanediphosphonate and pharmaceutically-acceptable salts thereof are substituted, respectively, for the disodium salt of methanehydroxydiphosphonate, with substantially similar results.

EXAMPLE II

A collecting vial containing 0.1 mg. of the sodium salt of reductic acid is placed at the eluate orifice of a pertechnetate-99m generator. Saline eluate is collected in the vial and completely dissolves the sodium reductate.

Approximately 5 ml. of the pertechnetate solution, with dissolved sodium reductate, is added to a pertechnetate reductant comprising 5.9 mg. of the sodium salt of ethane-1-hydroxy-1,1-diphosphonic acid and 0.16 mg. of stannous chloride. After thorough shaking, a stable skeletal imaging agent suitable for intravenous injection into a human patient is prepared. Excellent skeletal images are obtained when injected as in Example I.

In the above example, 5-methylreductic acid, 5-ethylreductic acid, 6-chloro-6-deoxyascorbic acid, 6-bromodeoxyascorbic acid, glucoascorbic acid, glucoascorbyl-6-octanoate, glucoascorbyl-7-hexanote, glucoascorbyl-7-palmitate, N-6-glucoascorbylacetamide, and nicotinic acid and nicotinamide complexes of reductic acid, 5-methylreductic acid, 5-ethylreductic acid, 6-bromo-6-deoxyascorbic acid, and 6-chloro-6-deoxyascorbic acid respectively, are used instead of the sodium salt of reductic acid, with substantialy similar results.

EXAMPLE III

An imaging composition is formulated with the following components:

| Component | Quantity |
|---|---|
| sodium pyrophosphate | 40.0 mg |
| sodium salt of 5-methylreductic acid | 0.20 mg |
| stannous citrate | 1.30 mg |

(The sodium pyrophosphate is as described above, and in U.S. Pat. No. 4,016,249, issued Apr. 5, 1979.)

The composition is prepared by simple admixture of the listed ingredients. A stable imaging agent is formed upon addition of about 5 ml of a pertechnetate-Tc99m solution, as described in Example I.

EXAMPLE IV

A stable imaging kit is formed with the following ingredients:

| Component | Quantity |
|---|---|
| monosodium salt of methaneamino diphosphonate | 3.0 mg |
| stannous chloride | 0.03 mg |
| sodium salt of 6-bromo-6-deoxy ascorbic acid | 0.70 mg |
| monosodium salt of methaneamino diphosphonate | 3.0 mg |
| stannous chloride | 0.03 mg |
| sodium salt of 6-bromo-6-deoxy ascorbic acid | 0.70 mg |
| glucose | 30.0 mg |

The kit is formed by dry blending the four ingredients. The composition is stored under nitrogen in a five milliliter vial fitted with a rubber septum. On addition of about 5 ml of pertechnetate-Tc99m, from a commercial technetium generator, with thorough shaking so as to completely dissolve all components, a stable imaging agent is found. Upon injection into a human subject, as described in Example I, excellent scintigraphic images are obtained.

In the foregoing Example, methane N-methylaminodiphosphonic acid, methane-N,N-dimethylaminodiphosphonic acid, methane hydroxyaminodiphosphonic acid, propane-1hydroxy-3-amino-1,1-diphosphonic acid, ethane-1-hydroxy-2-amino-1,1-diphosphonic acid, and the salts thereof, are substituted for the monosodium salt of methaneaminodiphosphonic acid, with substantially similar results. Also, in the foregoing example, stannous tartrate is used instead of stannous chloride, with substantially similar results.

We claim:
1. A composition, useful in the preparation of technetium-99m-based imaging agents, comprising:
   (a) a pertechnetate reductant; and
   (b) an effective amount, no more than about 25%, by weight, of a reductate stabilizer selected from the group consisting of compounds and mixtures of compounds having the formula:

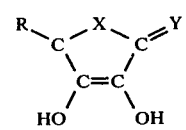

wherein X is CRR' O, or NR', R' is hydrogen, or lower alkyl, Y is oxygen, sulfur, nitrogen, or CH$_2$, R is hydrogen, lower alkyl, alkyl containing from 3 to 8 carbon atoms substituted with one or more hydroxy, halogen, amino, or thiol groups, alkyl containing from 1 to 8 carbon atoms halogen-substituted on the first and/or second carbon atom, lower alkenyl nicotinic acid and nicotinamide complexes thereof and pharmaceutically-acceptable salts, amides, and esters, thereof.

2. A composition, as in claim 1, wherein said reductate stabilizer is selected from the group consisting of 6-bromo-6-deoxyascorbic acid, 6-chloro-6-deoxyascorbic acid, 6-iodo-6-deoxyascorbic acid, and the pharmaceutically-acceptable salts and mixtures thereof.

3. A composition, as in claim 1, wherein said reductate stabilizer is selected from the group consisting of reductic acid, 4-methylreductic, 5-methlyreductic acid, 4-ethylreductic acid, 5-ethylreductic acid, and pharmaceutically-acceptable salts and mixtures thereof.

4. A composition as in claim 1, wherein said reductate stabilizer is selected from the group consisting of the nicotinic acid and nicotinamide complexes of 6-bromo-6-deoxyascorbic acid, 6-chloro-6-deoxyascorbic acid, 6-iodo-6-deoxyascorbic acid, reductic acid, 5-methylreductic acid, 5-ethylreductic acid, and mixtures thereof.

5. A composition, as in claim 1, comprising no more than 10%, by weight, of said reductate stabilizer.

6. A composition, as in claim 1, wherein said pertechnetate reductant is selected from the group consisting of the soluble stannous, chromous and ferrous salts.

7. A composition, as in claim 6, wherein said pertechnetate reductant is selected from the group consisting of stannous chloride, chromous chloride and ferrous sulfate.

8. A composition, as in claim 1, further comprising an organ-specific carrier.

9. A composition, as in claim 8, wherein the organ specific carrier is an organophosphonate.

10. A composition, as in claim 9, wherein said organophosphonate is selected from the group consisting of methanediphosphonic acid, methanehydroxydiphosphonic acid, ethane-1-hydroxy-1,1-diphosphonic acid, methaneaminidiphosphonic acid, methane-N-methylaminodiphosphonic acid, methane-N,N-dimethylamniodiphosphonic acid, propane-1-hydroxy-3-amino-1,1-diphosphonic acid, ethane-1-1-hydroxy-2-amino-1,1-diphosphonic acid, and the pharmaceutically-acceptable salts and mixtures thereof.

11. A composition, as in claim 10, wherein the pertechnetate reductant is stannous chloride, the organ-specific carrier is a sodium salt of methaneaminodiphosphonic acid, and the reductate stabilizer is 6-bromo-6-deoxyascorbic acid or a sodium salt thereof.

12. A composition, as in claim 10, wherein the pertechnetate reductant is stannous chloride, the organ-specific carrier is a sodium salt of methanediphosphonic acid, and the reductate stabilizer is 6-bromo-6-deoxyascorbic acid or a sodium salt thereof.

13. A composition, as in claim 10, wherein the pertechnetate reductant is stannous chloride, the organ-specific carrier is a sodium salt of methanehydroxydiphosphonic acid, and the reductate stabilizer is 6-bromo-6-deoxyascorbic acid or a sodium salt thereof.

14. A composition, as in claim 8, wherein the organ-specific carrier is a water-soluble inorganic phosphate.

15. A composition, useful in the preparation of technetium-99m-based radiographic imaging agents, comprising:

(a) an effective amount of a reductate stabilizer selected from group consisting of compounds and mixtures of compounds having the formula:

$$\begin{array}{c} R\diagdown_{C}\diagup^{X}\diagdown_{C}\diagup^{Y} \\ \diagdown_{C=C}\diagup \\ HO\diagup \quad \diagdown OH \end{array}$$

wherein X is CRR' O, or NR', R' is hydrogen, or lower alkyl, Y is oxygen, sulfur, nitrogen, or $CH_2$, R is hydrogen, lower alkyl, alkyl containing from 3 to 8 carbon atoms substituted with one or more hydroxy, halogen, amino, or thiol groups, alkyl containing from 1 to 8 carbon atoms halogen-substituted on the first and/or second carbon atom, lower alkenyl, nicotinic acid, nicotinamide complexes thereof and pharmaceutically-acceptable salts, amides, and esters thereof; dissolved in (b) an oxidized pertechnetate solution.

16. A composition, as in claim 15, comprising said oxidized pertechnetate solution having dissolved therein no more than about 0.1%, by weight, of said reductate stabilizer.

17. A method of preparing a stabilized technetium-99m-based imaging agent, comprising dissolving a reductate stabilizer selected from the group consisting of compounds and mixtures of compounds having the formula:

$$\begin{array}{c} R\diagdown_{C}\diagup^{X}\diagdown_{C}\diagup^{Y} \\ \diagdown_{C=C}\diagup \\ HO\diagup \quad \diagdown OH \end{array}$$

wherein X is CRR' O, or NR', R' is hydrogen, or alkyl containing from 1 to 8 carbon atoms, Y is oxygen, sulfur, nitrogen, or $CH_2$, R is hydrogen, lower alkyl, alkyl containing from 3 to 8 carbon atoms substituted with one or more hydroxy, halogen, amino, or thiol groups, alkyl containing from 1 to 8 carbon atoms halogen-substituted on the first and/or second carbon atom, lower alkenyl nicotinic acid and nicotinamide complexes thereof and pharmaceutically-acceptable salts, amides, and esters thereof; in an aqueous solution of radioactive technetium in the +3, +4, or +5 valence state.

18. A method of preparing a stabilized technetium-99m-based imaging agent, as in claim 17, wherein an organ-seeking carrier is included in the solution.

* * * * *